US00RE35748E

United States Patent [19]

Luck et al.

[11] E Patent Number: Re. 35,748

[45] Reissued Date of Patent: Mar. 17, 1998

[54] TREATMENTS EMPLOYING DRUG CONTAINING MATRICES FOR INTRODUCTION INTO CELLULAR LESION AREAS

[75] Inventors: Edward E. Luck; Dennis M. Brown, both of Menlo Park, Calif.

[73] Assignee: Matrix Pharmaceutical, Inc., Menlo Park, Calif.

[21] Appl. No.: 574,498

[22] Filed: Dec. 19, 1995

Related U.S. Patent Documents

Reissue of:

[64] Patent No.: Re. 33,375
Issued: Oct. 9, 1990
Appl. No.: 255,863
Filed: Oct. 11, 1988

Which is a Reissue of:

[64] Patent No.: 4,619,913
Issued: Oct. 28, 1986
Appl. No.: 736,496
Filed: May 21, 1985

U.S. Applications:

[63] Continuation-in-part of Ser. No. 615,008, May 29, 1984, abandoned.

[51] Int. Cl.[6] ..... A61K 9/00; A61K 9/22; A61K 9/26; A61K 31/28

[52] U.S. Cl. ..... 514/2; 514/801; 514/802; 514/965; 424/425; 424/484; 424/649

[58] Field of Search ..... 514/2, 801, 802, 514/965; 424/425, 484, 649

[56] References Cited

U.S. PATENT DOCUMENTS

| | | | |
|---|---|---|---|
| 2,589,210 | 3/1952 | McGinty | 514/6 |
| 4,177,263 | 12/1979 | Rosenberg et al. | 424/649 |
| 4,230,687 | 10/1980 | Sair et al. | 424/485 |
| 4,322,398 | 3/1982 | Reiner et al. | 424/425 |
| 4,347,234 | 8/1982 | Wahlig et al. | 424/426 |
| 4,349,530 | 9/1982 | Royer | 424/426 |
| 4,391,797 | 7/1983 | Folkman et al. | 424/425 |
| 4,407,787 | 10/1983 | Stemberger | 424/444 |
| 4,424,208 | 1/1984 | Wallace et al. | 514/21 |
| 4,536,387 | 8/1985 | Sakamoto et al. | 424/426 |

FOREIGN PATENT DOCUMENTS

| | | | |
|---|---|---|---|
| 83868 | 7/1983 | European Pat. Off. | 514/801 |
| 86627 | 8/1983 | European Pat. Off. | 424/405 |
| 56-122317 | 9/1981 | Japan . | |

OTHER PUBLICATIONS

Maugh, Science (1981), 212:1128–1129.

Macek et al, Abstracts of Immunology, 4109, p. 1053 (1977).

Miyata et al, Cancer Research (1983), 43:4670–4675.

McLaughlin et al, Cancer Research (1978), 38:1311–1316.

Bier et al, Cancer (1979), 44:1194–1200.

*Primary Examiner*—Jeffrey E. Russel
*Attorney, Agent, or Firm*—Flehr Hohbach Test Albritton & Herbert LLP; Richard F. Trecartin

[57] ABSTRACT

Treatment of cellular disorders involving abnormal solid cellular growths involves introduction of cytotoxic reagents dispersed in a physiologically acceptable proteinaceous matrix into the solid cellular growth or area of an existing or removed solid cellular growth. Enhanced effectiveness of the drug is observed, with reduced cytotoxic effects on cells distant from the site of introduction. Other drugs may be included to enhance therapeutic gain and reduce adverse affects to normal tissue.

16 Claims, No Drawings

TREATMENTS EMPLOYING DRUG CONTAINING MATRICES FOR INTRODUCTION INTO CELLULAR LESION AREAS

Matter enclosed in heavy brackets [ ] appears in the original patent but forms no part of the first and this reissue specification; matter printed in italics indicates the additions made by the first reissue. Matter enclosed in double heavy brackets [[ ]] appears in the first reissue patent but forms no part of this reissue specification; matter printed in bold face indicates the additions made by this reissue.

CROSS-REFERENCE TO RELATED APPLICATIONS

This is a continuation-in-part application of abandoned application Ser. No. 615,008, filed May 29, 1984, which disclosure is incorporated herein by reference.

BACKGROUND OF THE INVENTION

1. Field of the Invention

The treatment of many cellular disorders, for example, tumors, involves the use of cytotoxic drugs. These drugs exert their activity in a variety of ways, usually interfering with a cellular function essential for the replication and/or viability of the cell. In many, if not most, instances, the drug is not specific for the unnatural cell, but rather tends to exert its effectiveness due to the more rapid proliferation of the abnormal cell, as compared to normal cells. While many organs of the body of a mammalian host regenerate cells rather slowly, there are also other organs, particularly bone marrow, which involves rapid proliferation of stem cells. Therefore, the cytotoxic agents not only can detrimentally affect the slowly regenerating cells, but also have a particularly pernicious effect on the immune system.

Despite the many disadvantages and side effects of employing the strongly cytotoxic drugs, they have found extensive application, because they have provided positive results. However, there is substantial interest in being able to employ the drugs in a manner which directs their activity toward the abnormal cells, in an effort to protect sensitive normal cells, both in the vicinity of and distant from the abnormal cell growth, from the harmful effects of the drug.

2. Description of the Prior Art

U.S. Pat. Nos. 4,322,398; 4,347,234, 4,349,530; and 4,391,797 describe implants and controlled release of drugs. Implantation of drugs in lesions is described in Maugh, Science (1981) 212:1128–1129; Macek et al., Abstracts of Immunology, 4109, p. 1053, Miyata et al., Cancer Research (1983) 43:4670–4675; McLaughlin et al., Cancer Research (1978) 38:1311–1316; and Bier et al., Cancer (1979) 44:1194–1200.

SUMMARY OF THE INVENTION

Abnormal solid cellular growth, particularly tumors, or adjacent tissue that may contain tumor cells, are treated by injecting into the abnormal growth area or tissue suspected of containing tumor cells a sufficient mount of a cytotoxic drug dispersed in a stable flowable proteinaceous matrix. The resulting matrix substantially inhibits the migration of the drug from the site of injection, so as to maintain the primary effect of the drug in the region of injection. Migration can be further inhibited by the use of physiologically acceptable materials which enhance the binding of the drug to the matrix or which modify cellular properties or physiological responses to further regionalize the placement of drug at the injection site.

DESCRIPTION OF THE SPECIFIC EMBODIMENTS

Novel methods and compositions are provided for the chemotherapeutic treatment of solid abnormal tumors, cellular growth, or particularly, adjacent tissues which may contain abnormal tumor cells. The method employs a substantially uniform dispersion of a chemotherapeutic drug in a concentrated dispersion of a physiologically acceptable matrix, particularly a protein such as collagen, fibrinogen, or a derivative thereof, or other high molecular weight physiologically acceptable biodegradable composition, dispersed in a minor amount of a physiologically acceptable aqueous medium. The resulting amorphous mass is injected into the lesion, e.g., tumor, or lesion area, e.g., adjacent tissue, or in those situations where the minor has been removed, tissue adjacent to the previously removed tumor. The proteinaceous matrix is flowable for injection, but provides for stable placement, once injected into the tissue. That is, once injected the proteinaceous matrix adheres to the tissue and does not migrate significantly. The treatment may be employed with various solid tumors, including carcinomas and sarcomas. After injection, the drug is released into the immediate environment, so as to prevent substantial transportation of the drug to other sites, where its cytotoxic effect is undesirable. Thus, the circulating blood level of the drug remains low. In this way an enhanced therapeutic gain is achieved, that is, the cytotoxic effect on malignant cells is greater as compared to susceptible normal cells.

Illustrative of the various diseased states or therapeutic modes in which the subject invention may find application are: (1) Neoplasms in which local recurrence is typical and drug bioavailability is compromised, e.g., brain; (2) tumors in which suspected neoplastic cells remain in the tumor bed following surgical resection, e.g., breast; (3) tumors which are poor candidates for surgical or radiation management, e.g., head, neck, prostate, etc.; (4) adjunctive tumor therapy in combination with physical or non-chemical treatments, e.g., radiation and/or hyperthermia; (5) hyperproliferative diseases refractory to conventional therapy, e.g., psoriasis; (6) concurrent with systemic chemotherapy; (7) concurrent with systemic rescue, e.g., methotrexate, plus collagen matrix intra-tumorally, leucovorin i.v.

The subject compositions are amorphous, injectable and viscous, so as to substantially retain a localized position without significant flow from the site of administration. The compositions can flow under moderate pressure, but will not move significantly after being positioned at a particular site. The protein will be capable of binding the agents covalently or non-covalently, without preventing their therapeutic effect, while retaining the active agents at the site of introduction or retarding transfer of the active agents present from the site of introduction.

Preferably, the composition will be comprised of a significant amount of the matrix to provide the desired composition characteristics. The matrix may be comprised of individual or in combination peptides or proteins, e.g., structural proteins such as collagen and fibrinogen, or albumin or other protein which provides for stable placement, or combinations thereof. Of particular interest is collagen, fibrinogen or derivative thereof.

Proteinaceous compositions having at least about 5 weight percent, preferably at least about 10 weight percent, and up to 50 weight percent or more, are of particular interest when used in combination with thrombin or its enzymatic equivalent. In this way fibrinogen is enzymatically modified to fibrin to enhance the non-migratory property of the composition while forming a matrix of fibrils to further stabilize the composition.

The thrombin may be mixed with fibrinogen containing proteinaceous composition from a time immediately prior to use or shortly after injection. The amount of thrombin of about 1 to 1000 IU/mg employed will generally range from about 0.1 to 10 weight percent of the fibrinogen present, depending upon the time of use, the rate desired for solid matrix formation, the amount of other components, the effect of the drug on thrombin activity, and the like.

In addition to the matrix material will be one or more chemotherapeutic drugs, and a physiologically acceptable aqueous medium in which the proteinaceous composition is dispersed and the drug may be dissolved, dispersed, or complexed with the collagen. Other materials are preferably present to enhance the beneficial properties of the subject composition.

The proteinaceous, particularly collagenous or fibrinogen-containing, material which is used may be derived from any mammalian host source, such as bovine, porcine or human, or may be prepared, as available, by other techniques, e.g. recombinant DNA techniques. The collagen employed may be natural collagen or may be modified, such as tropocollagen, atropocollagen, or the like. The collagen may be non-immunogenic, immunogenic, or only slightly immunogenic.

Various methods of preparing collagen or derivatives thereof in purified form for administration to a mammalian host are known in the literature. These methods may be found in such patents as U.S. Pat. No. 3,949,073 and references cited therein. Of interest is bovine collagen which is purified and is obtained from young cows or calves. Purification will normally involve dispersion or precipitation from various media, e.g., dilute acetic acid. In some situations xenogeneic collagen is employed to enhance an immunogenic response in the area of injection or immunogenic adjuvants may be employed.

A wide variety of chemotherapeutic drugs may be employed individually or in combination. The drugs may be bound or unbound to the matrix, through such binding as complexation, salt formation, coordination complexes, or the like, but any binding should not result in significant diminution of the physiological activity of the drug. Various drugs may be employed which are used in chemotherapy and act as alkylating agents, enzyme inhibitors, proliferation inhibitors, lytic agents, DNA synthesis inhibitors, membrane permeability modifiers, DNA intercalators, antimetabolites, or the like. Illustrative drugs include chlorambucil, melphalan, busulfan, carmustine, lomustine, streptozotocin, thiotepa, decarbazine methotrexate, 5-fluorouracil, cytarabine, azaribine mercaptopurine, thioguanine, vinblastine, vincristine, antinomycin D, adriamycin, bleomycin, mithramycin, mitomycin C, L-asparaginase, cisplatin, procarbazine, prednisone, prednisilone, triamicinolone, testosterone, estrogen, insulins, and hydroxyurea. See Carter and Livingston, Drugs Available to Treat Cancer. In Principles of Cancer Treatment (Carter et al., eds.) Chapter 10, pp. 111–145, 1982, McGraw-Hill, Inc., N.Y. The drugs should not form non-enzymatically-labile bonds with the matrix material resulting in the loss of their therapeutic effect.

The drugs may be used individually or in combination, depending upon the nature of the drug, the tumor, and whether cooperative action is pharmacologically indicated. The drug composition can be further modified, by modifying the drug, particularly by bonds which allow for enzymatic cleavage, e.g., hydrolysis, or by introducing materials into the composition which will aid in the maintenance of the retention of the drug at the site of introduction.

Various techniques can be used for diminishing drug migration, for example, by coupling the drug with specific ligands, such as lipids, phospholipids, peptides, amino acids, sugars, or the like. These modifications will depend upon the individual drug, varying the solubility of the drug in the aqueous medium and providing for covalent or non-covalent interactions with the protein. In addition, various physiologically acceptable bulking agents or concentrating agents may be employed, which serve to provide for drug and protein interactions, with resulting reduction in the rate of drug release. Illustrative materials include inorganic substances, such as hydroxyapatite and organic substances such as carbohydrates, e.g, agarose and cellulose.

Other drugs for use in combination with the chemotherapeutic agents are drugs which retard the diffusion away of the chemotherapeutic agent, so as to reduce physiological insult and enhance therapeutic gain. Of particular interest are agents which restrict regional vasculature, either as to growth and/or passage opening, e.g., vasoconstrictive or sympathomimetic agents. These agents may include catechol amines, e.g., epinephrine and nor-epinephrine ergot alkaloids, prostaglandins, angiotensin or the like. Other agents for affecting tissue architecture include enzymes which can injure the stroma, such as the peptidases papain, chymopapain, trypsin, amylase, collagenase and chymotrypsin. Or, agents affecting cellular permeability may be employed, such as non-ionic detergents, e.g., Tween 80, amphotericin B, dimethylsulfoxide and anaesthetics, such as procaine.

In addition, the drug(s) can be employed encapsulated in liposomes or other controlled rate release compositions, which are included in the proteinaceous composition, so as to provide for separate and distinct rates of release of the drug. In this way, multiphasic compositions can be prepared, so as to provide for sustained release of the drug over long periods of time. Formation of liposomes with inclusion of various materials is described in Papahadjopoulos (1978) Annals of the N.Y. Academy of Science, 308; Gregoriadis and Allison (1980) Liposomes in Biological Systems, John Wiley and Sons, Leserman et al., Nature (1981) 293:226–228; Barhet et al, Supramol. Struct. Cell Bio. Chem. (1981) 16:243–258; and Heath et al., Science (1980) 255:8015–8018. Alternatively, other methods of encapsulation can be employed where the drug is encapsulated in a biodegradable substance, where the rate of release is related to the thickness of the biodegradable coat.

Besides using xenogeneic collagen, other materials may be included to enhance an immunogenic response, e.g., proliferation and invasion of macrophage, helper T-cells, etc. Illustrative adjuvants include Corynebacterium parvum, Bacillus Calmette-Guerin cell wall or cell wall skeleton preparations, Mycobacterium bovis strain, etc. See Miyata et al., Cancer Res. (1983) 43:4670–4675; Bier et al., Arch. Otorhinolaryngol, (1982) 236:245–255; and Mehanjhlin et al., Cancer Res. (1978) 38:1311–1316, whose relevant disclosure is incorporated herein by reference.

For enhancing cytotoxic activity various adjuvant materials may be incorporated into the matrix, such as radioactive pellet, e.g., radionuclides Technicium or Iridium; radiation sensitizers, e.g., misonidazole; repair inhibitors, e.g., methylated xanthines; bioreductive agents, which are activated only in hypoxic cells; immunomodifiers, such as interferons, lymphokines, such as interleukin-2; tumor growth inhibitors, such as tumor necrosis factor, tumor growth factor-β, etc., and/or angiographic contrast media.

As already indicated, the ratio of dry materials in the composition may vary widely. However, the amount of protein matrix material will usually be not less than 30% and not greater than about 95%, generally ranging from about from 40% to 90%, more usually ranging from about 50% to 90% by weight. Of this, preferably 10 to 100% will be collagen and/or fibrinogen. The chemotherapeutic drug(s) will normally be a liquid or solid, or provided in solid form and a generally range from at least about 0.1% by weight to up to about 50% by weight, more usually being from about 1% to 50% by weight, generally being from about 1% to 45% by weight of the proteinaceous material.

Other ancillary additives or agents will vary in total amount from about 0.005 to 15, usually from about 0.01 to 10 weight percent of the dry weight of the total composition.

The composition is uniformly dispersed in a physiologically acceptable aqueous medium, such as saline, phosphate buffered saline, distilled water, etc. The aqueous medium will be sufficient to provide for an amorphous dispersion capable of flowing under mild pressure. Usually, the liquid aqueous medium will be at least 90 weight percent of the entire composition, more usually at least 95% weight percent, and not more than about 99.8 weight percent, usually not more than about 99.5 weight percent, so as to provide a flowable mixture. The amount will vary depending upon the nature of the drug(s), the nature of the matrix material, the presence of other materials, and the like. The concentration of protein in the aqueous medium will range from about 5 to 75 mg/ml.

In addition to the major components, a number of minor components may also be included for a variety of purposes. These agents will for the most part impart properties which protect the stability of the composition, control the pH, or the like. Illustrative agents include phosphate or acetate buffers, methyl or propyl paraben, polyethylene glycols, etc. These agents generally will be present in less than about 2 weight percent of the total composition, usually less than about 1 weight percent, and individually may vary from about 0.001 weight percent to about 1 weight percent.

As already indicated, in some instances the drug will be encapsulated particularly in liposomes. Liposomes are prepared from a variety of lamellar-forming lipids including phospholipids, e.g., phosphatidylcholine, phosphatidylethanolamine, etc., gangliosides, sphingomyelins, steroids, e.g., cholesterol, etc. Usually, the weight of the lipids in relation to the weight of drug will range from 1 to 5 L of entrapped drug per mole of amphiphatic lipid.

The composition can be prepared by combining the various components in a sterile environment. The matrix will be provided in a convenient form, usually admixed with at least a portion of the total aqueous medium to be employed. The composition will be sufficiently workable that upon admixture of the other agents a uniform dispersion can be obtained. When collagen or derivative thereof is used, the collagenous material will normally be provided as a uniform dispersion of collagen fibrils in an aqueous medium, where the collagenous material will be from about 5 mg/ml to not more than 100, usually not more than 75 mg/ml. The drug may then be added to the collagenous dispersion with agitation to ensure the uniform dispersion of the drug in the resulting mixture. Other materials, as appropriate, may be added concomitantly or sequentially. After ensuring the uniform dispersion of the various components in the mixture, the mixture may be sterilized and sealed in appropriate container.

Sterilization will usually be achieved using aspetic conditions.

The subject composition can be used in the treatment of a wide variety of neoplastic lesions. Illustrative tumors include carcinomas, sarcomas and melanomas, such as basal cell carcinoma, squamous cell carcinoma, melanoma, soft tissue sarcoma, solar keratoses, Kaposi's sarcoma, cutaneons malignant lymphoma, Bowen's disease, Wilm's tumor, hepatomas, colorectals cancer, brain tumors; mycosis fungoides, Hodgkins lymphoma, polycythemia Vera, chronic granulocytic leukemia, lymphomas, oat cell sarcoma, etc.

The subject composition will be administered to a tumor to provide a cytotoxic amount of drug at the tumor site. The amount of cytotoxic drug administered to the tumor site will generally range from about 0.1 to 500, more usually about 0.5 to 300 mg/kg of host, depending upon the nature of the drug, size of tumor, and other considerations. The vasoconstrictive agents will generally be present in from 1 to 50 weight percent of the therapeutic agent. In view of the wide diversity of tumors, nature of tumors, effective concentrations of drug, relative mobility and the like, a definitive range cannot be specified. With each drug in each tumor, experience will provide an optimum level. One or more administrations may be employed, depending upon the lifetime of the drug at the tumor site and the response of the tumor to the drug. Administration may be by syringe, catheter or other convenient means allowing for introduction of a flowable composition into the tumor. Administration may be every three days, weekly, or less frequent, such as biweekly or at monthly intervals.

Illustrative of the manner of administration according to this invention would be administration of cis-diamino dichloro platinum. Drug concentrations in the matrix may vary from 0.01 to 50 mg/ml. Injection may be at one or more sites depending on the size of the lesion. Needles of about 1–2 mm diameter are convenient. For multiple injection templates with predrilled holes may be employed. The drug dose will normally be less than 100 mg/m$^2$ of patient.

The subject method finds particular advantage with tumors or lesions which are clinically relevant. The compositions provide therapeutic gain with tumors greater than 100 mm$^3$, more particularly, greater than 150 mm$^3$, in volume.

The subject method is also found to reduce local inflammation as a result of the drug administration. Therefore, local or adjacent tissues is less likely to be affected by the drug. Furthermore, due to the low migratory level of the drug from the site of placement, higher drug dosages can be administered to the site without adverse affects to normal tissue distant from the placement site or to lymphocytes.

The subject method finds advantage in conjunction with other forms of therapy. The lesions may be irradiated prior and/or subsequent to matrix administration. Dose rates may vary from about 20 to 250 rad/min, usually 50 to 150 rad/min, depending on the lesion, period of exposure, and the like. Hyperthermia (heat) may be used as an adjunctive treatment. Treatment will usually involve heating up to about and including 43° for about 5 to 100 min.

In order to demonstrate the subject invention, the following investigations were performed. A transplantable experimental murine fibrosarcoma ($2\times10^5$ RIF-1 cells) was grown intradermally in the flank of 5 month old female C3H mice (Bantin and Kingman, Fremont, CA). Cis-diamine dichloroplatinm (II) (cis-Pt) (Sigma Chemical Co., St. Louis, MO.) was dissolved in sterile saline at concentrations of 0.8, 1.6 and 3.2 mg/ml and mixed 1:1 with bovine collagen (BC) (36 mg/ml) in PBS 20 mM phosphate, 140 mM NaCl (Collagen Corp., Palo Alto, CA). Doses of 2, 4 and 8 mg/kg host of cis-Pt were delivered in 0.1 ml of the collagenous drug mixture to the center of the tumor growing in the flank (intratumorally, i.t.), and the tumor measured. The growth of a second uninjected tumor on the opposing flank of the same mouse was also measured. In addition, cis-Pt dissolved in PBS without collagen was administered intraperitoneally (i.p.) to other tumor-bearing mice (4 tumors/group) to monitor the effects on tumor growth of the drug without collagen. Furthermore, the effect of bovine collagen on tumor growth was also studied by injection of 0.1 ml of collagen, (18 mg/ml) into the experimental fibrosarcomas, as previously described. The growth of the tumors was monitored three times per week by caliper measurements of three perpendicular diameters of the tumor and calculating tumor volume from the formula $$V=\pi/6\times D_1\times D_2\times D_3.$$

The following Tables 1 and 2 indicate the results.

TABLE 1

Effect of cis-Pt-BC Fibrosarcoma Regrowth Delay

| Treatment Group | Route of Administration | cis-Pt Dose (mg/kg) | # Tumors Measured | Regrowth Delay* (Days) |
|---|---|---|---|---|
| Untreated (PBS) | i.p. | — | 4 | 6.3 ± 0.3** |
| cis-Pt | i.p. | 2 | 4 | 7.2 ± 0.1 |
| cis-Pt-BC | i.t. | 2 | 4 | 9.0 ± 1.1 |
| cis-Pt | i.p. | 4 | 6 | 9.1 ± 0.7 |
| cis-Pt-BC | i.t. | 4 | 4 | 9.9 ± 0.3 |
| cis-Pt | i.p. | 8 | 6 | 9.9 ± 1.0 |
| cis-Pt-BC | i.t. | 8 | 4 | 12.7 ± 1.2 |

*Regrowth Delay determined as the time (days) for tumors to grow to four times their initial treatment volume (150 $mm^3$). Increasing values indicate enchanced therapeutic effect.
**Mean ± S.E.

TABLE 2

Effect of cis-Pt-BC on the Growth of Uninjected Contralateral Fibrosarcoma

| Treatment Group | Route of Administration | cis-Pt Dose (mg/kg) | # Tumors Measured | Regrowth Delay* (Days) |
|---|---|---|---|---|
| Untreated (PBS) | i.p. | — | 4 | 6.3 ± 0.3** |
| cis-Pt | i.p. | 2 | 4 | 7.2 ± 0.1 |
| cis-Pt | i.t. | 2 | 4 | 9.5 ± 0.5 |
| uninjected contra | — | — | 4 | 9.3 ± 1.2 |
| cis-Pt-BC | i.t. | 2 | 4 | 9.0 ± 1.1 |
| uninjected contra | — | — | 4 | 7.2 ± 0.4 |
| cis-Pt | i.p. | 4 | 6 | 9.1 ± 0.7 |
| cis-Pt | i.t. | 4 | 4 | 10.3 ± 0.7 |
| uninjected contra | — | — | 4 | 8.9 ± 0.7 |
| cis-Pt-BC | i.t. | 4 | 4 | 9.9 ± 0.3 |
| uninjected contra | — | — | 4 | 7.4 ± 0.6 |
| cis-Pt | i.p. | 8 | 6 | 9.9 ± 1.0 |
| cis-Pt | i.t. | 8 | 4 | 11.5 ± 0.04 |
| uninjected contra | — | — | 4 | 9.9 ± 0.9 |

TABLE 2-continued

Effect of cis-Pt-BC on the Growth of Uninjected Contralateral Fibrosarcoma

| Treatment Group | Route of Administration | cis-Pt Dose (mg/kg) | # Tumors Measured | Regrowth Delay* (Days) |
|---|---|---|---|---|
| cis-Pt-BC | i.t. | 8 | 4 | 12.7 ± 1.3 |
| uninjected contra | — | — | 4 | 9.0 ± 1.1 |

*Regrowth Delay determined as the time (days) for tumors to grow to four times their initial treatment volume (150 $mm^3$).
**Mean ± S.E.

In the next study 5-fluorouracil (5-FU) (Sigma Chem. Co., St Louis, Mo.) with and without epinephrine (Sigma) suspended in saline by sonication (60 mg/ml) and mixed 1:1 with bovine collagen (BC) (Collagen Corp., Palo Alto, CA) (36 mg/ml) or normal saline. The subjects were 25 gm 12 week-old female C3H/He mice (Bantin and Kingman, Fremont, CA) bearing the transplatable experimental murine fibrosarcoma propagated intradermally as previously described.

When the tumors reached a volume of 150 $mm^3$, the mice were assigned randomly to the following groups (4–6 mice per group): (1) untreated controls; (2) 5-FU (100 mg/kg), i.p., 0.1 ml/mouse; (3) 5-FU (100 mg/kg), i.t., 0.1 ml/tumor; (4) 5-FU-BC (100 m.g 5-FU/kg dispersed in BC (18 mg/ml)), i.t., 0.1 ml/tumor, 5-FU-EPI-BC (100 mg 5-FU/kg) 5 mg EPI/kg dispersed in BC (18 mg/ml), i.t., 0.1 ml/tumor.

On day four post-treatment, white blood cells (wbc) were counted by sampling blood from the tail, dilution in Turk's solution and counting in a hemocytometer. On day eight post-treatment, skin reaction is overlying tissue was graded for untoward response.

The following Table 3 indicates the results.

TABLE 3

Effect of 5-Fluorouracil (5-FU) (100 mg/kg) – Bovine Collagen (BC) ± Epinephrine (EPI) (5 mg/kg) on Tumor Growth and Normal Tissue Response**

| Experimental Group (4–6 mice/group) | Tumor Regrowth Delay (days) | Untreated Contralateral Regrowth Delay (days) | White Blood Cells/$mm^3$ ($\times 10^3$) | Skin Reaction* |
|---|---|---|---|---|
| Untreated Controls | 6.3 ± 0.7*** | 6.3 ± 0.7 | 7.9 ± 1.6 | 1.0 ± 0.4 |
| 5-FU i.p. | 13.1 ± 1.4 | 13.1 ± 1.4 | 4.5 ± 0.6 | 0.7 ± 0.4 |
| 5-FU i.t. | 14.5 ± 0.9 | 11.1 ± 0.6 | 3.5 ± 0.5 | 0 |
| 5-FU-BC i.t. | 15.1 ± 3.3 | 8.6 ± 0.5 | 5.4 ± 2.2 | 1.3 ± 0.5 |
| 5-FU-EPI-BC i.t. | 17.7 ± 1.7 | 12.5 ± 1.2 | 5.0 ± 1.5 | 0 |

*Skin reaction. Evaluation of the skin overlying the tumor on Day 8 post injection.
The skin reaction is scored as follows:
0 = no effect;
1 = superficial inflammation;
2 = scab;
3 = ulcer.
**5-FU-EPI i.t. was lethal to the mouse.
***mean ± S.E.

In the next study doxorubicin-HCl (ADM) (Adriamycin) was studied using the above-described protocol. The adriamycin in distilled water (4.45 mg/ml) was mixed with 36 mg/ml bovine collagen (BC) 1:1 to yield a composition ratio of 2.25 mg adriamycin:18 mg BC/ml. Intraperitoneal injection of 15 mg/kg of adriamycin was lethal to 75% of the mice, while intratumoral injection was found to be nontoxic.

The following Table 4 indicates the results.

TABLE 4

Effect of Adriamycin (ADM) (15 mg/kg) – Bovine Collagen (BC) on Acute Animal Toxicity, Tumor Growth and Normal Tissue Response

| Experimental Group (4–6 mice/group) | Animal Survival[1] (%) | Tumor Regrowth Delay[2] Treated/Contralateral[3] (days) | White Blood Cells/mm$^3$ [4] ($\times 10^3$) | Skin Reaction[5] |
|---|---|---|---|---|
| Untreated Controls | 100 | 5.4 ± 0.2/5.4 ± 0.2 | 10.2 ± 1.7 | 1.3 ± 0.4 |
| Free ADM i.p. | 25 | 10.6 ± 1.6/10.6 ± 1.6 | 3.4 | 1.5 ± 0.5 |
| Free ADM i.t. | 100 | 13.7 ± 1.7/8.3 ± 0.75 | 4.1 ± 0.69 | 2.0 |
| ADM-BC i.t. | 100 | 10.6 ± 0.9/7.8 ± 1.3 | 6.8 ± 0.71 | 1.8 ± 0.2 |

[1]Animal survival after injection of ADM 15 mg/kg. Deaths usually resulted within 2 days after injection.
[2]Tumor Regrowth Delay (RD). Time (days) required for tumors to grow to 3× its original treatment volume (~150 mm$^3$). Increasing RD indicate increased tumor cell killing.
[3]Contralateral Tumor RD (CRD). Time (days) required for untreated contralateral tumors to grow to 3× its original treatment volume (~150 mm$^3$). Decreasing RD indicate enhanced regionalization of drug injected when compared to RD.
[4]White Blood Cells measured on Day 4 post injection by sampling from the tail of treatment mice.
[3]Skin reaction. Evaluation of the skin overlying the tumor on Day 8 post injection. The skin reaction is scored as follows:
0 = no effect;
1 = superficial inflammation;
2 = scab;
3 = ulcer;

In the next study vincristine (VCR) was dissolved in saline (0.6 mg/ml) by sonication and mixed 1:1 with bovine collagen (36 mg/ml). Otherwise, the procedure was the same. The following Table 5 indicates the results.

TABLE 5

Effect of Vincristine (VCR) (2 mg/kg) – Bovine Collagen (BC) on Tumor Growth and Normal Tissue Response

| Experimental Group (4–6 mice/group) | Tumor Regrowth Delay (days) | Untreated Contralateral Regrowth Delay (days) | White Blood Cells/mm$^3$ ($\times 10^3$) | Skin Reaction |
|---|---|---|---|---|
| Untreated Controls | 5.3 ± 0.2 | 5.3 ± 0.2 | 10.2 ± 1.7 | 1.3 ± 0.4 |
| VCR i.p. | 10.6 ± 2.0 | 10.6 ± 2.0 | 7.4 ± 1.3 | 0.6 ± 0.4 |
| VCR-BC i.t. | 10.2 ± 1.3 | 7.6 ± 1.1 | 9.4 ± 2.9 | 1.2 ± 0.5 |

In the next study a combination of bleomycin sulfate (Sigma Chemical Co., St. Louis, MO) (15 mg/kg) and epinephrine (5 mg/kg) employed in a bovine collagen composition were evaluated for antitumor effect in the transplantable experimental murine fibrosarcoma model previously described. The following Table 6 provides the results.

TABLE 6

Effect of Bleomycin Sulfate (BLM) (15 mg/kg) – Bovine Collagen (BC) ± Epinephrine (EPI) (5 mg/kg) on Tumor Growth and Normal Tissue Response

| Experimental Group (4–6 mice/group) | Tumor Regrowth Delay (days) | Untreated Contralateral Regrowth Delay (days) | White Blood Cells/mm$^3$ ($\times 10^3$) | Skin Reaction |
|---|---|---|---|---|
| Untreated Controls | 6.3 ± 0.7* | 6.3 ± 0.7 | 7.9 ± 1.6 | 1.0 ± 0.4 |
| BLM i.p. | 7.5 ± 0.9 | 7.5 ± 0.9 | 10.8 ± 1.8 | 1.5 ± 0.3 |
| BLM i.t. | 8.9 ± 0.6 | 7.0 ± 0.7 | 7.0 ± 1.3 | 2.3 ± 0.3 |
| BLM-BC i.t. | 9.4 ± 0.9 | 7.2 ± 0.1 | 8.0 ± 1.5 | 1.8 ± 0.3 |
| BLM-EPI-BC i.t. | 9.7 ± 0.6 | 7.2 ± 1.2 | 23.3 ± 10.7 | 1.5 ± 0.5 |

*mean ± S.E.

In another experiment the curative potential of drug matrix formulations was evaluated in the experimental murine fibrosarcoma model. Briefly, female C3H/He mice bearing a single experimental tumor produced as previously described were treated at weekly intervals with formulations containing 5-fluorouracil (50 mg/kg); bovine collagen BC (Collagen Corp., Palo Alto, CA); epinephrine (Sigma Chemical Co., St. Louis, MO); and PBS. WBC's were determined on Day 4 following each treatment cycle and skin reaction on Day 3 after each treatment cycle. Treatment was discontinued for all grops when 3 of 4 experiment groups reach 4×initial tumor volume. When tumors reached a volume of 150 mm$^3$ the mice were randomly assigned to the following groups:

1. Untreated controls
2. 5-FU-PBS i.p.; 5-FU (23 mg/ml) was combined 1:1 with PBS; 0.1 ml injected/mouse i.p.
3. 5-FU-PBS i.t.; 5-FU (23 mg/ml) was combined 1:1 with PBS; 0.1 ml injected/tumor i.t.
4. 5-FU-BC i.t.; 5-FU (23 mg/ml) was combined 1:1 with bovine collagen (36 mg/ml); 0.1 ml injected i.t.
5. 5-FU-BC-epi i.t.; 5-FU (23 mg/ml) was combined 1:1 with a bovine collagen (36 mg/ml) containing epinephrine (2.4 mg/ml); 0.1 ml injected i.t.

The results are shown in below in Table 7.

TABLE 7

Effect of 5-Fluorouracil (5-FU 50 mg/kg Administered on Days 0, 8 and 16) – Bovine collagen ± Epinephrine (5 mg/kg) on Tumor Growth and Normal Tissue

| Experimental Group | Tumor Regrowth 4× (days) | Contra-lateral RD 4× (days) | WBC D-12 | Skin Reaction D-8 |
|---|---|---|---|---|
| Untreated Controls | 6.3 ± 1.1 | — | 79 ± 13 | 2.6 ± 0.1 |
| 5-FU-PBS i.p. | 10.3 ± 1.3 | — | 109 ± 28 | 1.2 ± 1.1 |
| 5-FU-PBS i.t. | 14.9 ± 3.8 | — | 107 ± 25 | 1.0 ± 0.6 |
| 5-FU-BC i.t. | 11.2 ± 4.2 | — | 120 ± 21 | 1.6 ± 0.5 |
| 5-FU-BC-EPI i.t. | 26.0 ± 1.7 | — | 62 ± 6 | 1.4 ± 0.5 |

The results indicate that epinephrine (5 mg/Kg) used as a vascoactive modifier with low dose 5-FM-CM drug-matrix administered intratumorally (i.t.) in three weekly injections enhanced the antitumor effect of 5-FU by a factor of 2–2.5 with respect to i.p. treated minor regrowth delay.

In another experiment the influence of matrix composition on antitumor activity of 5-fluorouracil (100 mg/kg) was evaluated in the experimental murine fibrosarcoma model previously described. 5-FU (Sigma Chemical Co., St. Louis, MO) was combined as described below with bovine collagen BC (Collagen Corp., Palo Alto, CA); bovine fibronogen (95% clottable, Sigma); bovine thrombin (2000NIH units/mg, Sigma) and Ringer's Solution For Injection (RFI, Abbott Labs., North Chicago, IL). When tumors reached a volume of 150 $mm^3$ the mice (Bantin and Kingman, Fremont, CA) were assigned randomly to the following groups, (3–4 mice/group):

1. Untreated controls
2. Fibrinogen 30 mg/ml; fibrinogen (60 mg/ml) dispersed 1:1 with RFI containing 10 μl thrombin (1 NIH unit of activity/ml); 0.1 ml i.t.
3. 5-FU-Fibrinogen: 5-FU (36 mg/ml) combined 1:1 with the fibrinogen preparation described in 2 above, 0.1 ml i.t.
4. 5-FU-BC-Fibrinogen: 5-FU (36 mg/ml) combined 1:1 with a fibrinogen-BC preparation consisting of fibrinogen (30 mg/ml); BC (36 mg/ml) dispersed in RFI containing 1 NIH unit of thrombin activity/ml, 0.1 ml i.t.

The results are summarized in the following Table 8.

TABLE 8

Effect of Matrix Composition on Activity of 5-Fluorouracil (100 mg/kg)

| Experimental Group 3–4 mice/grp | Tumor Regrowth Delay 4× (days) | Untreated Contralateral RD 4× (days) | WBC/ $mm^3 \times 10^3$ | Skin Reaction |
|---|---|---|---|---|
| Untreated Controls | 6.3 ± 1.1 | 6.3 ± 1.1 | 79 ± 13 | 2.6 ± 0.1 |
| 5-FU-Fib (30 mg/ml) | 11.9 ± 1.7 | 7.7 ± 0.9 | 147 ± 38 | 1.3 ± 0.6 |
| Fib (30 mg/ml) | 5.5 ± 0.8 | 5.9 ± 0.5 | 276 ± 64 | 2.0 ± 0.0 |
| 5-FU-Fib (15 mg/ml) – BC (18 mg/ml) | 9.1 ± 0.8 | 8.2 ± 0.6 | 168 ± 27 | 2.0 ± 0.0 |

As evidenced from the above results, substantial advantages are obtained in therapeutic gain, both in the presence or absence of ancillary agents, when the therapeutic drugs are formulated as a flowable matrix in collagen and implanted in the lesion. The formulation retains the high chemotherapeutic activity of the chemotherapeutic agent, while substantially reducing the cytotoxic effect on white blood cells and inflammatory activity on adjacent epidermal tissue.

The evidence for reduced systemic exposure is apparent from the lack of immunosuppression, the relative absence of tumor regression on the contralateral uninjected tumor, and by the relative lack of untoward effect on overlaying normal tissue.

In the next experiment 5-fluorouracil-matrix implant in combination with X-rays was evaluated. Single RIF-1 tumors were grown on the back of female C3H mice (12–16 weeks) (Bantin and Kingman, Fremont, CA) as previously described. When the tumors reached volumes of 150 $mm^3$, they were divided into the following groups, (4–6 mice/group):

1. Untreated controls
2. X-rays (1000 rad.) alone
3. Collagen-matrix (CM) i.t. 5 min. before X-rays
4. 5-Fluorouracil (5-FU) (75 mg/Kg) i.p.
5. 5-FU-CM (75 mg/KG) i.t.
6. 5-FU i.p. 5 min before X-rays
7. 5-FU-CM i.t. 5 min before X-rays Tumor bearing mice were irradiated in lead jigs exposing only the tumor and overlying skin with a 250 kVp X-ray machine at a dose rate of 120 rad/min. The tumors of the treated and untreated mice were measured three times per week and assayed for regrowth delay and skin reactions as previously described.

The results are set forth in the following Table 9:

TABLE 9

Effect of 5-Fluorouracil (5-FU) (75 mg/Kg) – Collagen Matrix (CM) (30 mg/ml) Intralesional (i.t.) Implants in Conjunction with X-rays (1000 rad) on RIF-1 Tumor Regrowth Delay

| Experimental Group | 2× Tumor Regrowth Delay (days) | Skin Reaction |
|---|---|---|
| Untreated Controls | 3.1 ± 0.4 | 2 |
| 5-FU (i.p.) | 8.5 ± 1.1 | 2 |
| 5-FU-CM (i.t.) | 6.3 ± 0.5 | 2 |
| X-rays alone | 6.9 ± 0.3 | 2 |
| CM (i.t.) + X-rays | 6.0 ± 0.3 | 2 |
| 5-FU (i.p.) + X-rays | 12.6 ± 2.8 | 2 |
| 5-FU-CM (i.t.) + X-rays | 15.5 ± 0.9 | 2 |

The results indicate that in a combined modality setting intralesional (i.t.) administration of 5-FU-CM in conjunction with X-rays is comparable to X-rays with systemic (i.p.) 5-FU in terms of regrowth delay.

In the next study cis-DDP-matrix (DDP=cis-Pt) implant in combination with hyperthermia was evaluated. Single RIF-1 tumors were grown on the back of female C3H mice as previously described. When the tumors reached volumes of 150 $mm^3$, they were divided into the following groups (4–6 mice/group):

1. Untreated controls
2. Hyperthermia (43° C., 30 min) alone
3. Hyperthermia+collagen-matrix (CM)+epinephrine (epi) (2 mg/Kg)
4. cis-DDP (6 mg/Kg) i.p.
5. cis-DDP-CM-epi (i.t.)
6. cis-DDP (i.p.) 30 min before hyperthermia
7. cis-DDP-CM-epi (i.t.) 30 min before hyperthermia.

The tumor bearing mice were heated in a precision water bath with 30 gauge thermistor thermometry (±0.2° C.). The tumors of the treated and untreated mice were measured three times per week and assayed for regrowth delay as previously described.

The following Table 10 indicates the results:

TABLE 10

Effect of Local Hyperthermia (43° C. 30 min) on cis-DDP (6 mg/Kg) – Collagen Matrix (CM) (30 mg/ml) – Epinephrine (Epi) (2 mg/Kg) Intralesional (i.t.) Implants on RIF-1 Regrowth Delay

| Experimental Group | Tumor Regrowth Delay (2×) (2×) (days) |
|---|---|
| Untreated Controls | 3.5 ± 0.1 |
| Hyperthermia alone | 7.9 ± 1.3 |
| Hyperthermia + CM-Epi (i.t.) | 8.5 ± 0.5 |
| cis-DDP (i.p.) | 6.5 ± 1.5 |
| cis-DDP-CM-Epi (i.t.) | 10.0 ± 0.1 |
| cis-DDP (i.p.) 30 min before hyperthermia | 8.9 ± 0.8 |
| cis-DDP-CM-Epi (i.t.) 30 min before hyperthermia | 21.5 ± 2.3 |

The results indicate that local hyperthermia can enhance the effect of collagen matrix associated cis-DDP administered intratumorally. Collagen matrix (CM) with epinephrine (i.t.) alone with hyperthermia did not increase the antitumor effect of hyperthermia.

In accordance with the subject invention, improved neoplastic therapy is achieved by applying to an oncogenic lesion a composition comprising a chemotherapeutic drug composition, by itself or in combination with a vasoconstrictive agent uniformly dispersed in a collagenous aqueous dispersion and introducing the viscous amorphous mixture into the lesion. It is found that by employing the drug-collagenous composition, greatly enhanced localized drug concentration can be achieved. In addition, in view of the significant cytotoxic effects of drugs employed in chemotherapy, systemic exposure is substantially diminished. Therefore, high levels of cytotoxic drugs can be employed at the site of interest, while the remainder of the host is not exposed to significant levels of the drug. In addition, the drug pharmacokinetics are modified, due to modifications of the drug and/or interactions with the collagen, providing for a low level of the drug in the circulating blood. Finally, the lifetime of the drug can be extended due to protection by the collagenous material, reducing the rate of metabolic inactivation.

Although the foregoing invention has been described in some detail by way of illustration and example for purposes of clarity of understanding, it will be obvious that certain changes and modifications may be practiced within the scope of the appended claims.

What is claimed is:

1. A proteinaceous composition comprising from 30% to 95% of collagen and/or fibrinogen dispersed in an aqueous medium as an amorphous flowable mass at a concentration of from about 5 to 75 mg/ml and from about 0.1 to 50 weight percent based on said collagen and/or fibrinogen of a cytotoxic drug *or proliferation inhibitor*, wherein when said proteinaceous composition comprises collagen, said collagen is present as a uniform dispersion of collagen fibrils.

2. A composition according to claim 1, wherein said cytotoxic drug is cis-platinum, adriamycin, bleomycin, 5-fluorouracil or vincristine.

3. A proteinaceous composition [[according to claim 1, having]] comprising from 30% to 95% of collagen and/or fibrinogen dispersed in an aqueous medium as an amorphous flowable mass at a concentration of from about 5 to 75 mg/ml; from about 0.1 to 50 weight percent based on said collagen and/or fibrinogen of a cytotoxic drug or proliferation inhibitor and a vasoconstrictive amount of a vasoconstrictive drug.

4. A composition according to claim 3, wherein said [[vasoconstrictor]] vasoconstrictive drug is epinephrine or nor-epinephrine.

5. A method for treating a neoplastic *or hyperproliferative* lesion or surrounding tissue which comprises:

introducing at the site of said lesion a proteinaceous matrix composition capable of stable placement, consisting essentially [or] *of a* physiologically acceptable matrix forming collagen, fibrinogen or combination thereof, dispersed in an aqueous medium as an amorphous flowable mass including at least one cytotoxic drug *or proliferation inhibitor* uniformly dispersed in said composition[;]][:];

whereby said [[drug]] cytotoxic drug or proliferation inhibitor is slowly released into the [[immediate environment]] neoplastic or hyperproliferative lesion or surrounding tissue avoiding significant levels of [[the drug]] said cytotoxic drug or proliferation inhibitor at sites distant from the site of introduction.

6. A method according to claim 5, wherein said proteinaceous composition is a collagen fibril dispersion.

7. A method according to claim 6, wherein said [[drug]] cytotoxic drug or proliferation inhibitor is at least one of cis-platinum, adriamycin, [[5fluorouracil]] 5-fluorouracil, bleomycin, vincristine, or methotrexate.

8. A method according to claim 7, wherein said composition includes a sufficient amount of a [[vasoconstrictor]] vasoconstrictive drug to constrict capillaries in the vicinity of said lesion.

9. A method according to claim 8, wherein said [[vasoconstrictor]] vasoconstrictive drug is epinephrine or nor-epinephrine.

10. A method according to claim 7, wherein said [[drug]] cytotoxic drug or proliferation inhibitor is cis-platinum.

11. A method according to claim 7, wherein said [[drug]] cytotoxic drug or proliferation inhibitor is 5-fluorouracil.

12. A method according to claim 5, comprising the additional step of treating said lesion [[size]] site with radiation or heat.

*13. A proteinaceous composition comprising from 30% to 95% of collagen and/or fibrinogen dispersed in an aqueous medium as an amorphous flowable mass at a concentration of from about 5 to 75 mg/ml and from about 0.1 to 50 weight percent based on said collagen and/or fibrinogen of a cytotoxic drug*, wherein when said proteinaceous composition comprises collagen, said collagen is present as a uniform dispersion of collagen fibrils.

*14. A proteinaceous composition comprising from 30% to 95% of collagen and/or fibrinogen dispersed in an aqueous medium as an amorphous flowable mass at a concentration of from about 5 to 75 mg/ml and from about 0.1 to 50 weight percent based on said collagen and/or fibrinogen of a proliferation inhibitor*, wherein when said proteinaceous composition comprises collagen, said collagen is present as a uniform dispersion of collagen fibrils.

*15. A method for treating a neoplastic lesion or surrounding tissue which comprises:*

*introducing at the site of said lesion a proteinaceous matrix composition capable of stable placement consisting essentially of a physiologically acceptable matrix forming collagen, fibrinogen or combination thereof, dispersed in an aqueous medium as an amorphous flowable mass, including at least one cytotoxic drug or proliferation inhibitor uniformly dispersed in said composition;*

*whereby said drug* cytotoxic drug or proliferation inhibitor *is slowly released into the immediate environment* neoplastic lesion or surrounding tissue *avoiding significant levels of the drug* said cytotoxic drug or proliferation inhibitor *at sites distant from the site of introduction.*

*16. A method for treating a hyperproliferative lesion or surrounding tissue which comprises:*

*introducing at the site of said lesion a proteinaceous matrix composition capable of stable placement consisting essentially of a physiologically acceptable matrix forming collagen, fibrinogen or combination thereof, dispersed in an aqueous medium as an amorphous flowable mass, including at least one cytotoxic drug or proliferation inhibitor uniformly dispersed in said composition;*

*whereby said drug* cytotoxic drug or proliferation inhibitor *is slowly released into the immediate environment* hyperproliferative lesion or surrounding tissue *avoiding significant levels of the drug* said cytotoxic drug or proliferation inhibitor *at sites distant from the site of introduction.*

* * * * *

UNITED STATES PATENT AND TRADEMARK OFFICE

CERTIFICATE OF CORRECTION

PATENT NO. : Re. 35,748

DATED : March 17, 1998

INVENTOR(S) : LUCK et al.

It is certified that error appears in the above-indentified patent and that said Letters Patent is hereby corrected as shown below:

At [54], delete "DRUG CONTAINING" and insert therefor --DRUG-CONTAINING--.

Column 1, line 1, delete "DRUG CONTAINING" and insert therefor --DRUG-CONTAINING--.

Column 1, line 61, delete "mount" and insert therefor --amount--.

Column 2, line 19, delete "minor" and insert therefor --tumor--.

Column 4, line 54, immediately following "response," delete the new paragraphing.

Column 4, line 66, delete "pellet" and insert therefor --pellets--.

Column 5, line 14, delete "a" and insert therefor --will--.

Column 6, line 67 - column 7, line 1, delete "dichloroplatinm" and insert therefor --dichloroplatinum--.

Column 11, line 3, delete "minor" and insert therefor --tumor--.

Column 14, line 11, of claim 15 delete "*drug* cytotoxic drug" and insert therefor "**[[*drug*]] cytotoxic drug**".

UNITED STATES PATENT AND TRADEMARK OFFICE

CERTIFICATE OF CORRECTION

PATENT NO. : Re. 35,748

DATED : March 17, 1998

INVENTOR(S) : LUCK et al.

It is certified that error appears in the above-indentified patent and that said Letters Patent is hereby corrected as shown below:

Column 14, line 12-13, of claim 15, delete "*immediate environment* neoplastic" and insert therefor "[[*immediate environment*]] neoplastic".

Column 14, line 14, of claim 15, delete "*the drug* said" and insert therefor "[[*the drug*]] said".

Column 14, line 11, of claim 16, delete "*drug* cytotoxic drug" and insert therefor "[[*drug*]] cytotoxic drug".

Column 14, line 12-13, of claim 16, delete "*immediate environment* neoplastic" and insert therefor "[[*immediate environment*]] neoplastic".

Column 14, line 14, of claim 16, delete "*the drug* said" and insert therefor "[[*the drug*]] said".

Signed and Sealed this

Twenty-eighth Day of July, 1998

*Attest:*

*Attesting Officer*

Bruce Lehman

BRUCE LEHMAN

*Commissioner of Patents and Trademarks*